(12) United States Patent
Giranda et al.

(10) Patent No.: US 9,623,009 B2
(45) Date of Patent: Apr. 18, 2017

(54) VELIPARIB IN COMBINATION WITH CARBOPLATIN AND PACLITAXEL FOR THE TREATMENT OF NON-SMALL CELL LUNG CANCER IN SMOKERS

(71) Applicant: AbbVie Inc., North Chicago, IL (US)

(72) Inventors: Vincent Giranda, Gurnee, IL (US); Gary Gordon, Highland Park, IL (US); Mark D. McKee, Chicago, IL (US); Jane Qian, Libertyville, IL (US); Qin Qin, Lincolnshire, IL (US)

(73) Assignee: AbbVie, Inc., North Chicago, IL (US)

( * ) Notice: Subject to any disclaimer, the term of this patent is extended or adjusted under 35 U.S.C. 154(b) by 0 days.

(21) Appl. No.: 14/855,621

(22) Filed: Sep. 16, 2015

(65) Prior Publication Data

US 2016/0074368 A1    Mar. 17, 2016

Related U.S. Application Data

(60) Provisional application No. 62/051,040, filed on Sep. 16, 2014.

(51) Int. Cl.
| | |
|---|---|
| *A61K 31/4184* | (2006.01) |
| *A61K 31/555* | (2006.01) |
| *A61K 31/337* | (2006.01) |
| *A61K 31/282* | (2006.01) |
| *A61K 31/4188* | (2006.01) |

(52) U.S. Cl.
CPC ........ *A61K 31/4184* (2013.01); *A61K 31/282* (2013.01); *A61K 31/337* (2013.01); *A61K 31/4188* (2013.01); *A61K 31/555* (2013.01)

(58) Field of Classification Search
CPC ................ A61K 31/282; A61K 31/337; A61K 31/4188; A61K 31/4184; A61K 31/555
See application file for complete search history.

(56) References Cited

U.S. PATENT DOCUMENTS

2014/0187537 A1 * 7/2014 Brandes ................. A61K 33/24
514/215

FOREIGN PATENT DOCUMENTS

| WO | 2008030887 A2 | 3/2008 |
|---|---|---|
| WO | 2010139069 A1 | 12/2010 |

OTHER PUBLICATIONS

Bosse et. al., Cancer Research, 2012, American Association for Cancer Research, vol. 72(15), pp. 3753-3763.*
Albert J.M., et al., "Inhibition of Poly(Adp-Ribose)Polymerase Enhances Cell Death and Improves Tumor Growth Delay in Irradiated Lung Cancer Models," Clinical Cancer Research, 2007, vol. 13 (10), pp. 3033-3042.
International Search Report and Written Opinion for Application No. PCT/US2015/050367, mailed on Nov. 26, 2015, 13 pages.
Isakoff S.J., et al., "Abstract OT2-3-07: A Randomized, Phase 2 Study of the Poly (ADP-ribose) Polymerase (PARP) Inhibitor Veliparib (ABT-888) in Combination with Temozolomide (TMZ) or in Combination with Carboplatin (C) and Paclitaxel (P) Versus Placebo plus C/P in subjects with BRCA1 or BRACA2 Mutation and Metastatic Breast Cancer," Cancer Research, 35th Annual CTRC-AACR San Antonio Breast Cancer Symposium,2012, vol. 72 (24 Suppl), p. 1.
Ramalingam S., et al., "A Randomized, Double-Blind, Phase 2 Trial of Veliparib (ABT-888) with Carboplatin and Paclitaxel in Previously Untreated Metastatic or Advanced Non-Small Cell Lung Cancer," Metastatic Non-Small Cell Lung Cancer, 2014, vol. 90 (5).

* cited by examiner

*Primary Examiner* — Sarah Pihonak
(74) *Attorney, Agent, or Firm* — Quarles & Brady LLP (57) ABSTRACT

This invention pertains to a method for the treatment of non-small cell lung cancer in a subject who is a smoker, comprising administering to the subject an effective amount of 2-[(2R)-2-methylpyrrolidin-2-yl]-1H-benzimidazole-4-carboxamide (veliparib or ABT-888), or a pharmaceutically acceptable salt thereof, in combination with carboplatin and paclitaxel.

5 Claims, 7 Drawing Sheets

VELIPARIB IN COMBINATION WITH CARBOPLATIN AND PACLITAXEL FOR THE TREATMENT OF NON-SMALL CELL LUNG CANCER IN SMOKERS

RELATED APPLICATION INFORMATION

This application claims the benefit of U.S. Provisional Patent Application Ser. No. 62/051,040, filed on Sep. 16, 2014, the contents of which are herein incorporated by reference in their entirety.

FIELD OF THE INVENTION

This invention pertains to the use of veliparib in combination with carboplatin and paclitaxel in the treatment of smokers with non-small cell lung cancer.

BACKGROUND OF THE INVENTION

Lung cancer accounts for more deaths than any other cancer in both men and women. An estimated 159,260 deaths, accounting for about 27% of all cancer deaths, are expected to occur in the United States in 2014 (American Cancer Society. *Cancer Facts & Figures* 2014. Atlanta: American Cancer Society, 2014). Lung cancer is broadly classified into two types: non-small cell lung cancer and small cell lung cancer. Non-small cell lung cancer (NSCLC) comprises 80-85% of lung cancer cases in the United States. NSCLC comprises three major types: (i) Squamous cell carcinoma, which begins in squamous cells, that are thin, flat cells that look like fish scales. Squamous cell carcinoma is also called epidermoid carcinoma; (ii) Large cell carcinoma, which begins in several types of large lung cells; (iii) Adenocarminoma, which begins in the cells that line the alveoli of the lung and make substances such as mucus. Other less common types of NSCLC include pleomorphic carcinoma, carcinoid tumor and unclassified carcinoma.

Poly(ADP-ribose)polymerse (PARP) or poly(ADP-ribose)synthase (PARS) is a nuclear enzyme that has an essential role in recognizing DNA damage, facilitating DNA repair, controlling RNA transcription, mediating cell death, and regulating immune response. PARP activity is required for the repair of single-stranded DNA breaks through the base excision repair pathways. Cancer cells are often deficient in double-stranded DNA-repair capability, and are therefore more dependent on PARP directed single-stranded DNA-repair than are normal cells. Consequently, inhibition of PARP enhances the anti-tumor effects of DNA-damaging agents in many cancer cells.

Platinum-based chemotherapy regimens are the current standard of care for subjects with metastatic or advanced non-small cell lung cancer (NSCLC). Veliparib (ABT-888, 2-[(2R)-2-methylpyrrolidin-2-yl]-1H-benzimidazole-4-carboxamide) is a potent, orally bioavailable PARP inhibitor that enhances the efficacy of platinum-containing DNA damaging therapies in some pre-clinical models, and veliparib has been safely combined with full dose carboplatin and paclitaxel in human clinical trials. The present invention describes the use of veliparib in combination with carboplatin and paclitaxel in the treatment of smokers with non-small cell lung cancer.

BRIEF SUMMARY OF THE INVENTION

The present invention pertains to a method for the treatment of non-small cell lung cancer in a subject who is a smoker, comprising administering to the subject an effective amount of a PARP inhibitor in combination with carboplatin and paclitaxel. In one embodiment, the present invention pertains to a method for the treatment of non-small cell lung cancer in a subject who is a smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel.

DETAILED DESCRIPTION OF THE INVENTION

Definitions

The terms "treat", "treating" and "treatment" refer to a method of alleviating or abrogating a disease and/or its attendant symptoms.

The term "subject" is defined herein to include animals such as mammals, including, but not limited to, primates (e.g., humans), cows, sheep, goats, horses, dogs, cats, rabbits, rats, mice and the like.

In preferred embodiments, the subject is a human.

The terms "patient" and "subject" are used herein interchangeably.

"Effective amount" refers to the amount sufficient to induce a desired biological, pharmacological, or therapeutic outcome in a subject. A therapeutically effective amount of a compound can be employed as a zwitterion or as a pharmaceutically acceptable salt. A therapeutically effective amount means a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

The term "PFS" means progression-free survival.

The term "OS" means overall survival.

The term "current smoker" means a subject having ≥100 smoking events in his or her lifetime and smoking within one year prior to commencement of therapy.

The term "former smoker" means a subject having ≥100 smoking events in his or her lifetime but has not had any smoking events within the past year.

The term "never smoker" means a subject with <100 smoking events in his or her lifetime.

The term "ever smoker" means former smokers and current smokers combined.

The term "heavy smoker" means a current or former smoker with ≥39 pack-years.

The term "light smoker" means a current or former smoker with <39 pack-years.

The term "smoker" means a subject classified as one or more of the following: current smoker, heavy smoker, and/or cotinine high patient.

The term "pack-years" means patient reported years of smoking times patient reported packs of cigarettes smoked per day. One pack of cigarettes is defined as a commercially available package in the United States with typically 20 cigarettes per peck of any available size or strength. The median number of pack-years for ever smokers described below was 39.

The terms "chemical evidence of smoking" and "cotinine high patient" mean all patients with cotinine >10 ng/mL.

The term "hazard ratio" (HR) is a measure of the risk of an event occurring under the conditions of the experiment compared to the risk of the event occurring under control conditions. A hazard ratio of 0.5 confers that the risk of an event (such as tumor progression or death) with the treatment tested in a clinical trial is half of the risk with standard therapy. Also, with a hazard ratio of 0.5, events under study (such as tumor progression or death) take twice as long to occur in the treated group as in the control group, assuming exponential survival distribution.

The term "DNA damage" is an art-recognized term and is used herein to refer to any chemical changes to DNA, including, but not limited to, damaged (oxidized, alkylated, hydrolyzed, adducted, or cross-linked) bases, mutations, single-stranded DNA breaks, and double-stranded DNA breaks. Particularly, the DNA damage in a subject of the present invention is induced or associated with cigarette consumption that produces or generates free radicals and oxidants that induce or lead to oxidative damage to DNA. Identification, quantification or measurement of DNA damage in a current smoker, a former smoker, or a never smoker, or DNA damage profile mapping in a current smoker, a former smoker or a never smoker can be carried out by one skill in the art using known technologies. One skilled in the art would also be able to compare DNA profiles between different subjects and determine the similarity of DNA damage profile between the subjects.

In one embodiment, the present invention relates to a method for the treatment of non-small cell lung cancer in a subject who is a current smoker, or with a DNA damage profile similar to that of a subject who is a current smoker, comprising administering to the subject an effective amount of a PARP inhibitor in combination with carboplatin and paclitaxel. In another embodiment, the present invention relates to a method for the treatment of non-small cell lung cancer in a subject who is a current smoker, comprising administering to the subject an effective amount of a PARP inhibitor in combination with carboplatin and paclitaxel. In another embodiment, the present invention relates to a method for the treatment of non-small cell lung cancer in a subject with a DNA damage profile similar to that of a subject who is a current smoker, comprising administering to the subject an effective amount of a PARP inhibitor in combination with carboplatin and paclitaxel.

In one embodiment, the present invention relates to a method for the treatment of non-small cell lung cancer in a subject who is a heavy smoker, or with a DNA damage profile similar to that of a subject who is a heavy smoker, comprising administering to the subject an effective amount of a PARP inhibitor in combination with carboplatin and paclitaxel. In another embodiment, the present invention relates to a method for the treatment of non-small cell lung cancer in a subject who is a heavy smoker, comprising administering to the subject an effective amount of a PARP inhibitor in combination with carboplatin and paclitaxel. In another embodiment, the present invention relates to a method for the treatment of non-small cell lung cancer in a subject with a DNA damage profile similar to that of a subject who is a heavy smoker, comprising administering to the subject an effective amount of a PARP inhibitor in combination with carboplatin and paclitaxel.

In one embodiment, the present invention relates to a method for the treatment of non-small cell lung cancer in a subject who is a cotinine high patient, or with a DNA damage profile similar to that of a subject who is a cotinine high patient, comprising administering to the subject an effective amount of a PARP inhibitor in combination with carboplatin and paclitaxel. In another embodiment, the present invention relates to a method for the treatment of non-small cell lung cancer in a subject who is a cotinine high patient, comprising administering to the subject an effective amount of a PARP inhibitor in combination with carboplatin and paclitaxel. In another embodiment, the present invention relates to a method for the treatment of non-small cell lung cancer in a subject with a DNA damage profile similar to that of a subject who is a cotinine high patient, comprising administering to the subject an effective amount of a PARP inhibitor in combination with carboplatin and paclitaxel.

In one embodiment, the present invention relates to a method for the treatment of non-small cell lung cancer in a subject who is a smoker, or with a DNA damage profile similar to that of a subject who is a smoker, comprising administering to the subject an effective amount of a PARP inhibitor in combination with carboplatin and paclitaxel. In another embodiment, the present invention relates to a method for the treatment of non-small cell lung cancer in a subject who is a smoker, comprising administering to the subject an effective amount of a PARP inhibitor in combination with carboplatin and paclitaxel. In another embodiment, the present invention relates to a method for the treatment of non-small cell lung cancer in a subject with a DNA damage profile similar to that of a subject who is a smoker, comprising administering to the subject an effective amount of a PARP inhibitor in combination with carboplatin and paclitaxel.

In one embodiment, the present invention relates to a method for the treatment of non-small cell lung cancer in a subject who is a current smoker, or with a DNA damage profile similar to that of a subject who is a current smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject who is a current smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject with a DNA damage profile similar to that of a subject who is a current smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel.

In one embodiment, the present invention relates to a method for the treatment of non-small cell lung cancer in a subject who is a heavy smoker, or with a DNA damage profile similar to that of a subject who is a heavy smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject who is a heavy smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject with a DNA damage profile similar to that of a subject who is a heavy smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel.

In one embodiment, the present invention relates to a method for the treatment of non-small cell lung cancer in a subject who is a cotinine high patient, or with a DNA damage profile similar to that of a subject who is a cotinine high patient, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject who is a cotinine high patient, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject with a DNA damage profile similar to that of a subject who is a cotinine high patient, comprising administering to the subject an effective amount of 2-[(2R)-2-methylpyrrolidin-2]-yl-1H-benzimidazole-4-carboxamide, or a pharmaceutically acceptable salt thereof; in combination with carboplatin and paclitaxel.

In one embodiment, the present invention relates to a method for the treatment of non-small cell lung cancer in a subject who is a smoker, or with a DNA damage profile similar to that of a subject who is a smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject who is a smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel. In another embodiment, the present invention relates to a method for the treatment of non-small cell lung cancer in a subject with a DNA damage profile similar to that of a subject who is a smoker, comprising administering to the subject an effective amount of 2-[(2R)-2-methylpyrrolidin-2-yl]-1H-benzimidazole-4-carboxamide, or a pharmaceutically acceptable salt thereof, in combination with carboplatin and paclitaxel.

In one embodiment, the present invention relates to a method for the treatment of a disease in a subject who is a current smoker, or with a DNA damage profile similar to that of a subject who is a current smoker, comprising administering to the subject an effective amount of a PARP inhibitor in combination with carboplatin and paclitaxel. In another embodiment, the present invention relates to a method for the treatment of a disease in a subject who is a current smoker, comprising administering to the subject an effective amount of a PARP inhibitor in combination with carboplatin and paclitaxel. In another embodiment, the present invention relates to a method for the treatment of a disease in a subject with a DNA damage profile similar to that of a subject who is a current smoker, comprising administering to the subject an effective amount of a PARP inhibitor in combination with carboplatin and paclitaxel.

In one embodiment, the present invention relates to a method for the treatment of a disease in a subject who is a heavy smoker, or with a DNA damage profile similar to that of a subject who is a heavy smoker, comprising administering to the subject an effective amount of a PARP inhibitor in combination with carboplatin and paclitaxel. In another embodiment, the present invention relates to a method for the treatment of a disease in a subject who is a heavy smoker, comprising administering to the subject an effective amount of a PARP inhibitor in combination with carboplatin and paclitaxel. In another embodiment, the present invention relates to a method for the treatment of a disease in a subject with a DNA damage profile similar to that of a subject who is a heavy smoker, comprising administering to the subject an effective amount of a PARP inhibitor in combination with carboplatin and paclitaxel.

In one embodiment, the present invention relates to a method for the treatment of a disease in a subject who is a cotinine high patient, or with a DNA damage profile similar to that of a subject who is a cotinine high patient, comprising administering to the subject an effective amount of a PARP inhibitor in combination with carboplatin and paclitaxel. In another embodiment, the present invention relates to a method for the treatment of a disease in a subject who is a cotinine high patient, comprising administering to the subject an effective amount of a PARP inhibitor in combination with carboplatin and paclitaxel. In another embodiment, the present invention relates to a method for the treatment of a disease in a subject with a DNA damage profile similar to that ofa subject who is a cotinine high patient, comprising administering to the subject an effective amount of a PARP inhibitor in combination with carboplatin and paclitaxel.

In one embodiment, the present invention relates to a method for the treatment of a disease in a subject who is a smoker, or with a DNA damage profile similar to that of a subject who is a smoker, comprising administering to the subject an effective amount of a PARP inhibitor in combination with carboplatin and paclitaxel. In another embodiment, the present invention relates to a method for the treatment of a disease in a subject who is a smoker, comprising administering to the subject an effective amount of a PARP inhibitor in combination with carboplatin and paclitaxel. In another embodiment, the present invention relates to a method for the treatment of a disease in a subject with a DNA damage profile similar to that of a subject who is a smoker, comprising administering to the subject an effective amount of a PARP inhibitor in combination with carboplatin and paclitaxel.

In one embodiment, the subject has a primary solid malignancy which is non-small cell lung cancer (NSCLC). In another embodiment, the NSCLC can be squamous cell carcinoma, or non-squamous cell carcinoma. In another embodiment, the NSCLC is squamous cell carcinoma. In another embodiment, the NSCLC is non-squamous cell carcinoma.

In one embodiment, the subject has lung cancer with a DNA damage profile similar to that of a subject who is a current smoker. In another embodiment, the subject has lung cancer with a DNA damage profile similar to that of a subject who is a heavy smoker. In another embodiment, the subject has lung cancer with a DNA damage profile similar to that of a subject who is a cotinine high patient. In another embodiment, the subject has lung cancer with a DNA damage profile similar to that of a subject who is a smoker. In another embodiment, the subject has a disease with a DNA damage profile similar to that of a subject who is a current smoker. In another embodiment, the subject has a disease with a DNA damage profile similar to that of a subject who is a heavy smoker. In another embodiment, the subject has a disease with a DNA damage profile similar to that of a subject who is a cotinine high patient. In another embodiment, the subject has a disease with a DNA damage profile similar to that of a subject who is a smoker.

This invention also is directed, in part, to all salts of 2-[(2R)-2-methylpyrrolidin-2-yl]-1H-benzimidazole-4-carboxamide and methods of their use.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a current smoker, or with a DNA damage profile similar to that of a subject who is a current smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a current smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject with a DNA damage profile similar to that of a subject who is a current smoker.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a heavy smoker, or with a DNA damage profile similar to that of a subject who is a heavy smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a heavy smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject with a DNA damage profile similar to that of a subject who is a heavy smoker.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a cotinine high patient, or with a DNA damage profile similar to that of a subject who is a cotinine high patient. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a cotinine high patient. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject with a DNA damage profile similar to that of a subject who is a cotinine high patient. Preferably, the composition additionally comprises, or is additionally combined with, carboplatin and paclitaxel.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a smoker, or with a DNA damage profile similar to that of a subject who is a smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject who is a smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a subject with a DNA damage profile similar to that of a subject who is a smoker. Preferably, the composition additionally comprises, or is additionally combined with, carboplatin and paclitaxel.

In one embodiment, the present invention relates to a composition comprising 2-[(2R)-2-methylpyrrolidin-2-yl]-1H-benzimidazole-4-carboxamide-4-carboxamide, or a pharmaceutically acceptable salt thereof, for use in a method for the treatment of non-small cell lung cancer in a subject who is a current smoker, or with a DNA damage profile similar to that of a subject who is a current smoker. In another embodiment, the present invention relates to a composition comprising 2-[(2R)-2-methylpyrrolidin-2-yl]-1H-benzimidazole-4-carboxamide, or a pharmaceutically acceptable salt thereof for use in a method for the treatment of non-small cell lung cancer in a subject who is a current smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of non-small cell lung cancer in a subject with a DNA damage profile similar to that of a subject who is a current smoker.

In one embodiment, the present invention relates to a composition comprising 2-[(2R)-2-methylpyrrolidin-2-yl]-1H-benzimidazole-4-carboxamide, or a pharmaceutically acceptable salt thereof for use in a method for the treatment of non-small cell lung cancer in a subject who is a heavy smoker, or with a DNA damage profile similar to that of a subject who is a heavy smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of non-small cell lung cancer in a subject who is a heavy smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of non-small cell lung cancer in a subject with a DNA damage profile similar to that of a subject who is a heavy smoker.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of non-small cell lung cancer in a subject who is a cotinine high patient, or with a DNA damage profile similar to that of a subject who is a cotinine high patient. In another embodiment, the present invention relates to a composition comprising 2-[(2R)-2-methylpyrrolidin-2-yl)]-1H-benzimidazole-4-carboxamide, or a pharmaceutically acceptable salt thereof, for use in a method for the treatment of non-small cell lung cancer in a subject who is a cotinine high patient. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of non-small cell lung cancer in a subject with a DNA damage profile similar to that of a subject who is a cotinine high patient. Preferably, the composition additionally comprises, or is additionally combined with, carboplatin and paclitaxel.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of non-small cell lung cancer in a subject who is a smoker, or with a DNA damage profile similar to that of a subject who is a smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of non-small cell lung cancer in a subject who is a smoker. In another embodiment, the present invention relates to a composition comprising 2-[(2R)-2-methylpyrrolidin-2-yl]-1H-benzimidazole-4-arboxamide, or a pharmaceutically acceptable salt thereof, for use in a method for the treatment of non-small cell lung cancer in a subject with a DNA damage profile similar to that of a subject who is a smoker. Preferably, the composition additionally comprises, or is additionally combined with, carboplatin and paclitaxel.

In one embodiment, the present invention relates to a composition comprising 2-[(2R)-2-methylpyrrolidin-2-yl]-H-benzimidazole-4-carboxamide, or a pharmaceutically acceptable salt thereof, for use in a method for the treatment of a disease in a subject who is a current smoker, or with a DNA damage profile similar to that of a subject who is a current smoker. In another embodiment, the present invention relates to a composition comprising 2-[(2R)-2-methyl-pyrrolidin-2-yl]-1H-benzimidazole-4-carboxamide, or a pharmaceutically acceptable salt thereof, for use in a method for the treatment of a disease in a subject who is a current smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject with a DNA damage profile similar to that of a subject who is a current smoker.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject who is a heavy smoker, or with a DNA damage profile similar to that of a subject who is a heavy smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject who is a heavy smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject with a DNA damage profile similar to that of a subject who is a heavy smoker.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject who is a cotinine high patient, or with a DNA damage profile similar to that of a subject who is a cotinine high patient. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject who is a cotinine high patient. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject with a DNA damage profile similar to that of a subject who is a cotinine high patient. Preferably, the composition additionally comprises, or is additionally combined with, carboplatin and paclitaxel.

In one embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject who is a smoker, or with a DNA damage profile similar to that of a subject who is a smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject who is a smoker. In another embodiment, the present invention relates to a composition comprising 2-[(2R)-2-methylpyrrolidin-2-yl]-1H-benzimidazole-4-carboxamide, or a pharmaceutically acceptable salt thereof, for use in a method for the treatment of a disease in a subject with a DNA damage profile similar to that of a subject who is a smoker. Preferably, the composition additionally comprises, or is additionally combined with, carboplatin and paclitaxel.

A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible.

The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of 2-[(2R)-2-methylpyrrolidin-2-yl]-1H-benzimidazole-4-carboxamide can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of 2-[(2R)-2-methylpyrrolidin-2-yl]-1H-benzimidazole-4-carboxamide include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

This invention also is directed, in part, to all compositions of 2-[(2R)-2-methylpyrrolidin-2-yl]-1H-benzimidazole-4-carboxamide and methods of their use. 2-[(2R)-2-methylpyrrolidin-2-yl]-1H-benzimidazole-4-carboxamide may be administered with or without an excipient. Excipients include, but are not limited to, encapsulators and additives such as absorption accelerators, antioxidants, binders, buffers, costing agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising 2-[(2R)-2-methylpyrrolidin-2-yl]-1H-benzimidazole-4-carboxamide to be administered orally include, but are not limited to, agar, alginic acid, aluminum hydroxide, benzyl alcohol, benzyl benzoate, 1,3-butylene glycol, carbomers, castor oil, cellulose, cellulose acetate, colloidal silica, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, microcrystalline cellulose, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, titanium dioxide, tragacanth, tetrahydrofurfuryl alcohol, triglycerides, water, mixtures thereof and the like.

Total daily dose of the compositions of the invention to be administered to a human or other mammal host in single or divided doses may be in amounts, for example, from about 0.0001 to about 300 mg/kg body weight daily and more usually about 1 to about 300 mg/kg body weight. The dose, from about 0.0001 to about 300 mg/kg body, may be given once or multiple times per day.

In one embodiment of the invention, the dose of 2-[(2R)-2-methylpyrrolidin-2-yl]-1H-benzimidazole-4-carboxamide, or a pharmaceutically acceptable salt or solvate thereof, is in the range of 20 to 600 ms or in the range of 60 to 400 mg. In a further embodiment of the invention, the dose of 2-[(2R)-2-methylpyrrolidin-2-yl]-1H-benzimidazole-4-carboxamide or a pharmaceutically acceptable salt or solvate thereof, is about 30 mg, 50 mg, 80 mg, 100 mg, 120 mg, 150 mg, 200 mg, 240 mg, or 300 mg. In one embodiment, the dose is administered multiple times per day. In one embodiment, the dose is administered once a day or twice a day. In one embodiment, the dose is administered twice a day. In one embodiment, the dose is 120 mg, and is administered twice a day.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Throughout this application, the term "about" is used to indicate that a value includes the inherent variation of error for the device, the method being employed to determine the value, or the variation that exists among the study subjects. When used in the context of dosing, the term "about" is used to indicate a value of ±10% from the reported value, preferably a value of ±5% from the reported value.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Example

A Phase 2, randomized, double-blind, multi-center study was conducted evaluating the efficacy, safety, and tolerability of veliparib in combination with carboplatin and paclitaxel versus placebo in combination with carboplatin and paclitaxel in subjects with documented metastatic or advanced non-small cell lung cancer (NSCLC) as first-line chemotherapy. Patients were randomized in a 2:1 ratio to either veliparib+carboplatin/paclitaxel or placebo+carboplatin/paclitaxel. Patient randomization was stratified by histology (squamous cell versus non-squamous cell), and smoking history (current smoker versus never smoked versus past smoker). Screening procedures and baseline radiographic tumor assessments were performed within 21 days prior to the first day veliparib/placebo was administered. Radiographic tumor assessments were conducted every 6 weeks and were sent to a central imaging center for review. Dosing of oral veliparib/placebo (120 mg) began 2 days prior to the start of the carboplatin/paclitaxel and was given twice a day (BID) for 7 days. All subjects received carboplatin (AUC 6 mg/mL/min) and paclitaxel (200 mg/m2) starting on Day 3 of each cycle via IV infusion. Patients continued to receive veliparib/placebo in combination with carboplatin/paclitaxel for up to a maximum 6 cycles of treatment if no unacceptable toxicity or progression of NSCLC occurred. All subjects were to remain on study until reaching a protocol defined event of disease progression. Patients who completed 6 cycles of treatment remained on study/off study drugs until reaching an event of disease progression. Chemotherapy or biological therapy (maintenance therapy) was not allowed until disease progression. Patients who experienced toxicities due to carboplatin/paclitaxel or veliparib may have been given a delay in the dosing schedule or a dose modification.

All subjects had Metastatic or Advanced Non-Small Cell Lung Cancer. Patients included in the study were: 1) ≥18 years of age; 2) had life expectancy >12 weeks; 3) had cytologically or histologically confirmed NSCLC; 4) had metastatic or advanced NSCLC that was not amenable to surgical resection or radiation with curative intent at time of study Screening; 5) had at least 1 unidimensional measurable NSCLC lesion on a CT scan; 6) had no history of brain metastases or evidence of primary CNS tumors as demonstrated by a baseline MRI; 7) had an Eastern Cooperative Oncology Group (ECOG) Performance Score of 0-1; 8) had adequate bone marrow, renal and hepatic function as follows: Absolute neutrophil count (ANC) ≥1,500/mm3 (1.5×109/L), Platelets ≥100,000/mm3 (100×109/L, Hemoglobin ≥9.0 g/dL (1.4 mmol/L), serum creatinine ≥1.5×ULN or creatinine clearance >50 ml/min, AST and ALT ≤2.5× ULN unless liver metastases are present, then AST and ALT<5.0×ULN; bilirubin ≤1.5×ULN.

Patients excluded from the study had a known hypersensitivity to paclitaxel or to other drugs formulated with polyethoxylated castor oil (Cremophor); had a known hypersensitivity to platinum compounds; had peripheral neuropathy≥grade 2; had a known EGFR mutation of exon 19 deletion or L858R mutation in exon 21; had received prior systemic anti-cancer therapy for metastatic NSCLC; had received adjuvant chemotherapy ≤12 months prior to entry; had received anti-cancer Chinese medicine or anti-cancer herbal remedies within 14 days of study entry; had undergone External Beam Radiation Therapy (EBRT)≤8 weeks prior to study entry; had clinically significant and uncontrolled major medical condition(s); were pregnant or lactating; or had previously been treated with a PARP inhibitor.

PFS was defined as the number of days from the date that the subject was randomized to the date the subject experienced an event of disease progression (as determined by a central imaging center) or to the date of death (all causes of mortality) if disease progression was not reached. All events of disease progression (as determined by the central imaging center) were included, regardless of whether the event occurred while the subject was still taking veliparib/placebo or had previously discontinued veliparib/placebo. However, if a disease progression event occurred after a subject missed two or more consecutive disease progression assessments; the subject was censored at the last disease progression assessment prior to the missing disease progression assessments. All events of death were included for subjects who had not experienced disease progression, provided the death occurred within 42 days of the last disease assessment. If the subject did not have an event of disease progression (as determined by the central imaging center) nor had the subject died, the subject's data was censored at the date of the subject's last disease assessment. PFS results were reported at the point in the study with 78 PPS events (pre-defined primary endpoint of the study).

Time to death (overall survival, OS) for a given subject was defined as the number of days from the date that the subject was randomized to the date of the subjects death. All events of death were included, regardless of whether the event occurred while the subject was still taking veliparib/placebo or had previously discontinued veliparib/placebo. If a subject did not die during the study, then the data wee censored at the date when the subject was last known to be alive. OS results are reported at the point in the study with 90 OS events (from an analysis that was planned for review of mature OS data).

Key Results.

Stratification factors for randomization were histology (squamous versus non-squamous) and smoking history (current smoker versus former smoker versus never smoker). The current smoker strata showed the most benefit from the addition of veliparib to standard chemotherapy (Table 1).

TABLE 1

PFS and OS for Pre-Specified Subgroups

| | Placebo/ Carboplatin/ Paclitaxel | Valiparib/ Carboplatin/ Paclitaxel | HR (95% Adjusted[a] CI) |
|---|---|---|---|
| PFS (months) | | | |
| Squamous | 4.1 | 6.1 | 0.32 (0.14, 0.73) |
| Non-squamous | 5 | 4.3 | 0.76 (0.41, 1.42) |
| Current smoker | 3.3 | 5.6 | 0.30 (0.16, 0.57) |
| Former smoker | NA | 6 | 0.77 (0.19, 3.11) |
| Never smoker | 5.6 | 6.4 | 1.10 (0.24, 4.98) |
| OS (months) | | | |
| Squamous | 8.5 | 10.3 | 0.76 (0.41, 1.41) |
| Non-squamous | 11.1 | 12.6 | 0.63 (0.33, 1.19) |
| Current smoker | 5.4 | 12.5 | 0.44 (0.25, 0.77) |
| Former smoker | NA | 8.6 | 1.25 (0.40, 3.96) |
| Never smoker | 11.4 | 13.1 | 0.65 (0.16, 2.61) |

[a]From Cox proportional hazards model adjusting for gender and ECOG performance status.

Figure 1:
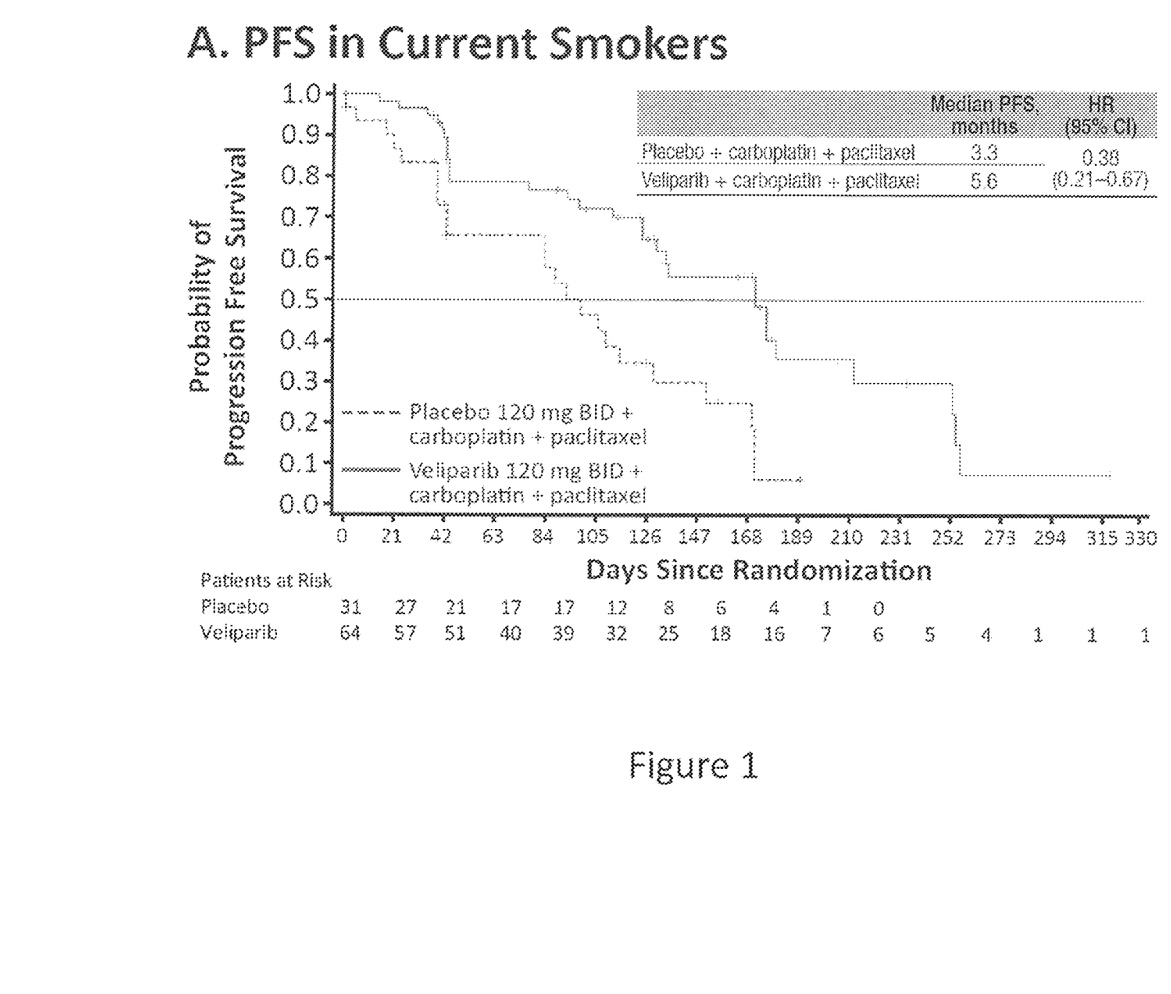
FIG. 1 shows progression-free survival (PFS) in currant smokers, placebo vs. veliparib, in human subjects.
Figure 2:
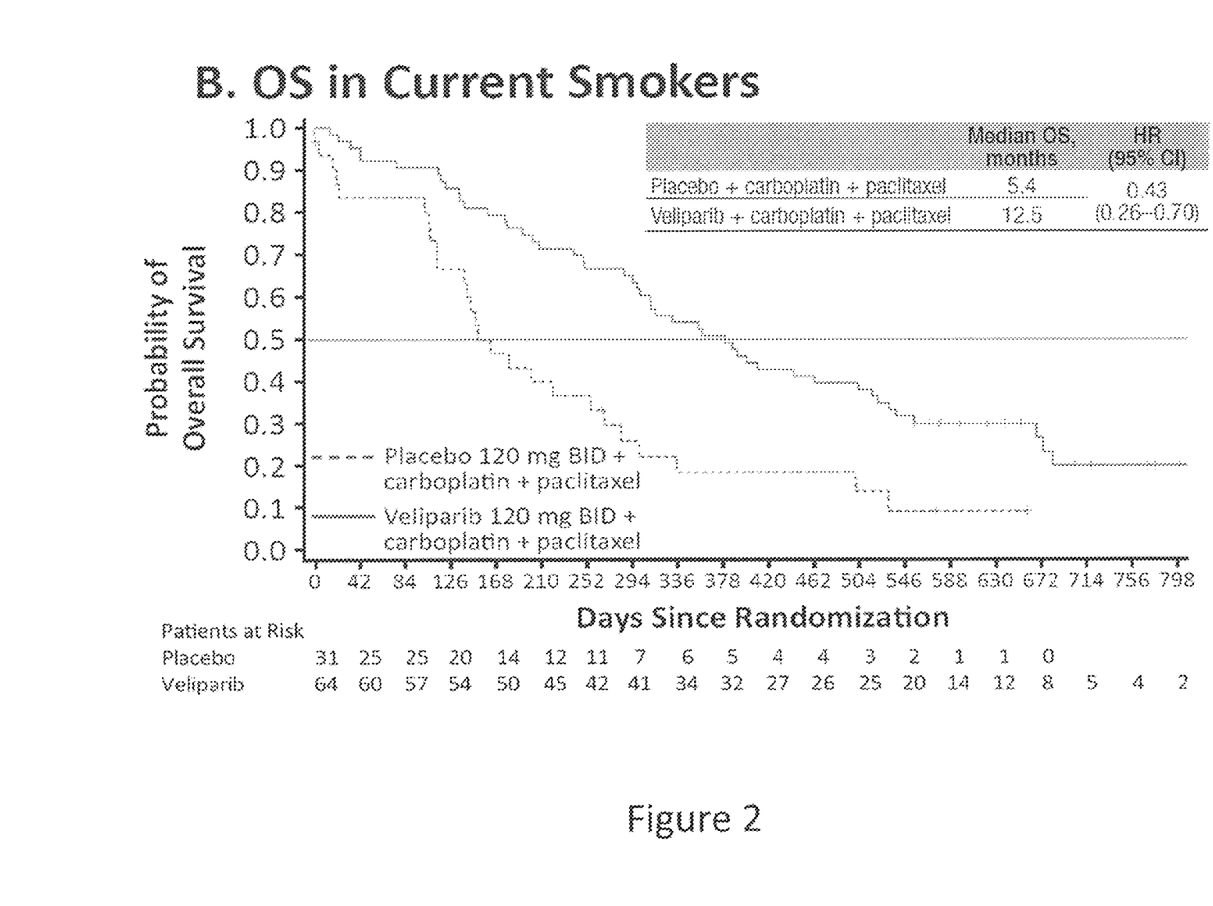
FIG. 2 shows overall survival (OS) in current smokers, placebo vs. veliparib, in human subjects.
Figure 3:
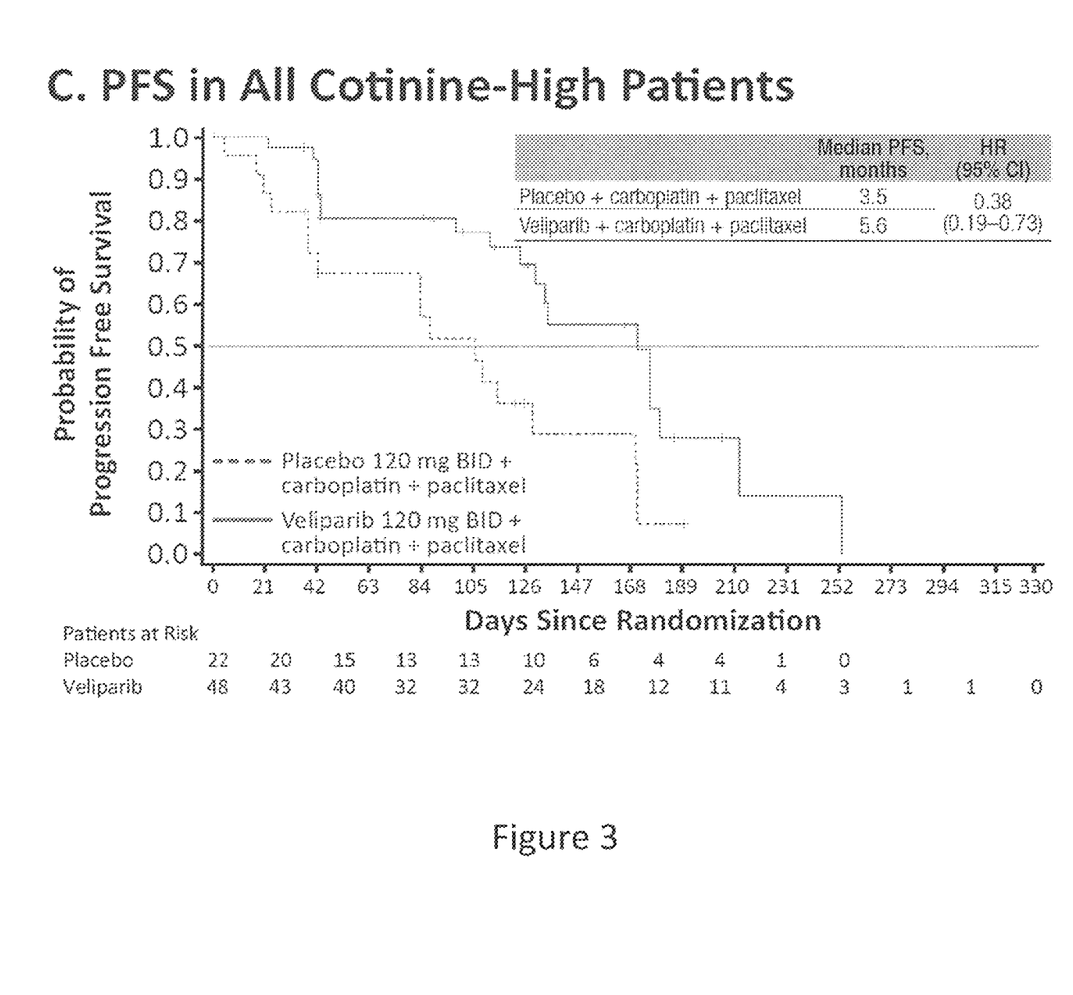
FIG. 3 shows progression-free survival (PFS) in cotinine high patients, placebo vs. veliparib, in human subjects.
Figure 4:
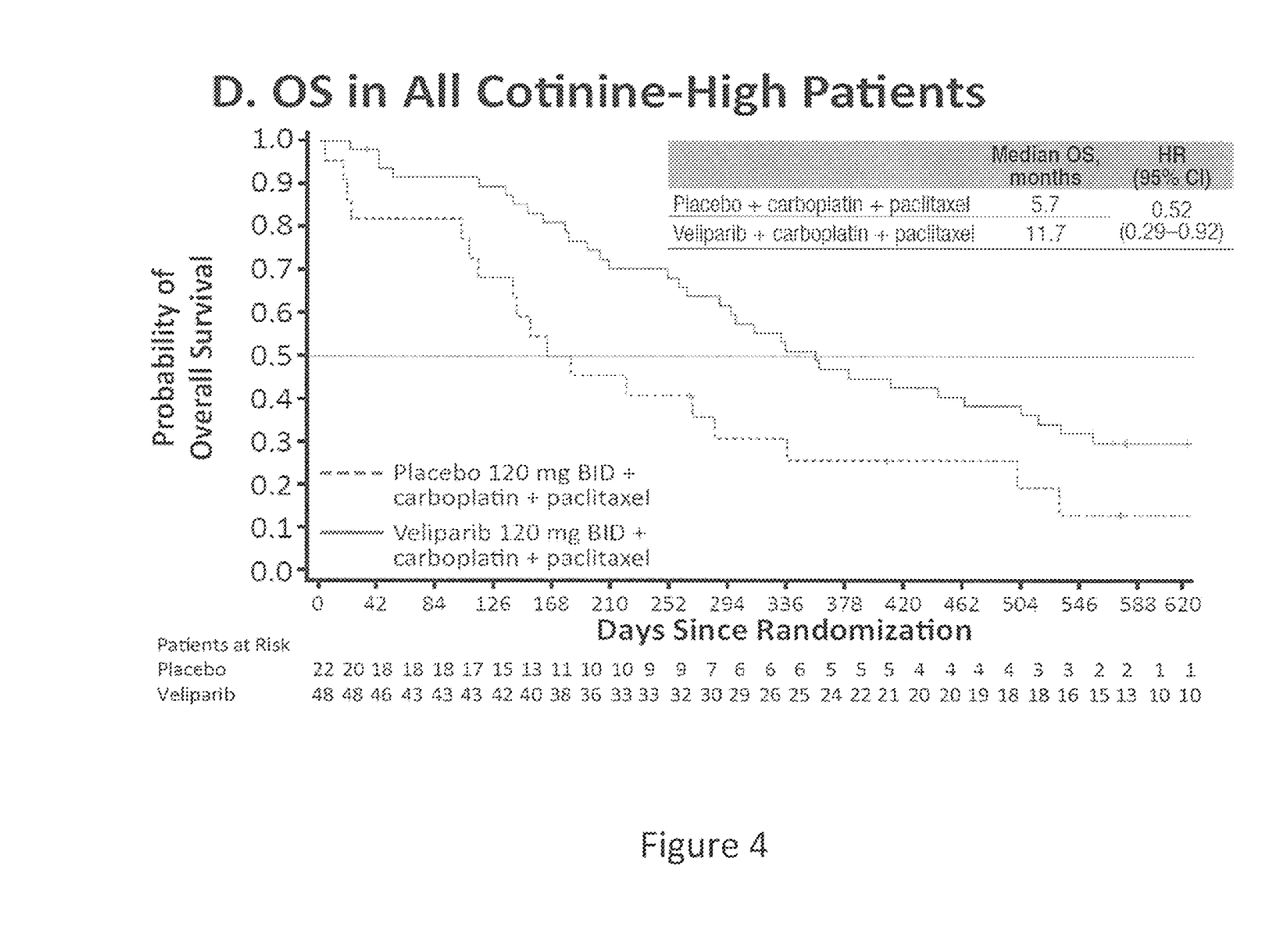
FIG. 4 shows overall survival (OS) in cotinine high patients, placebo vs. veliparib, in human subjects.
Figure 5:
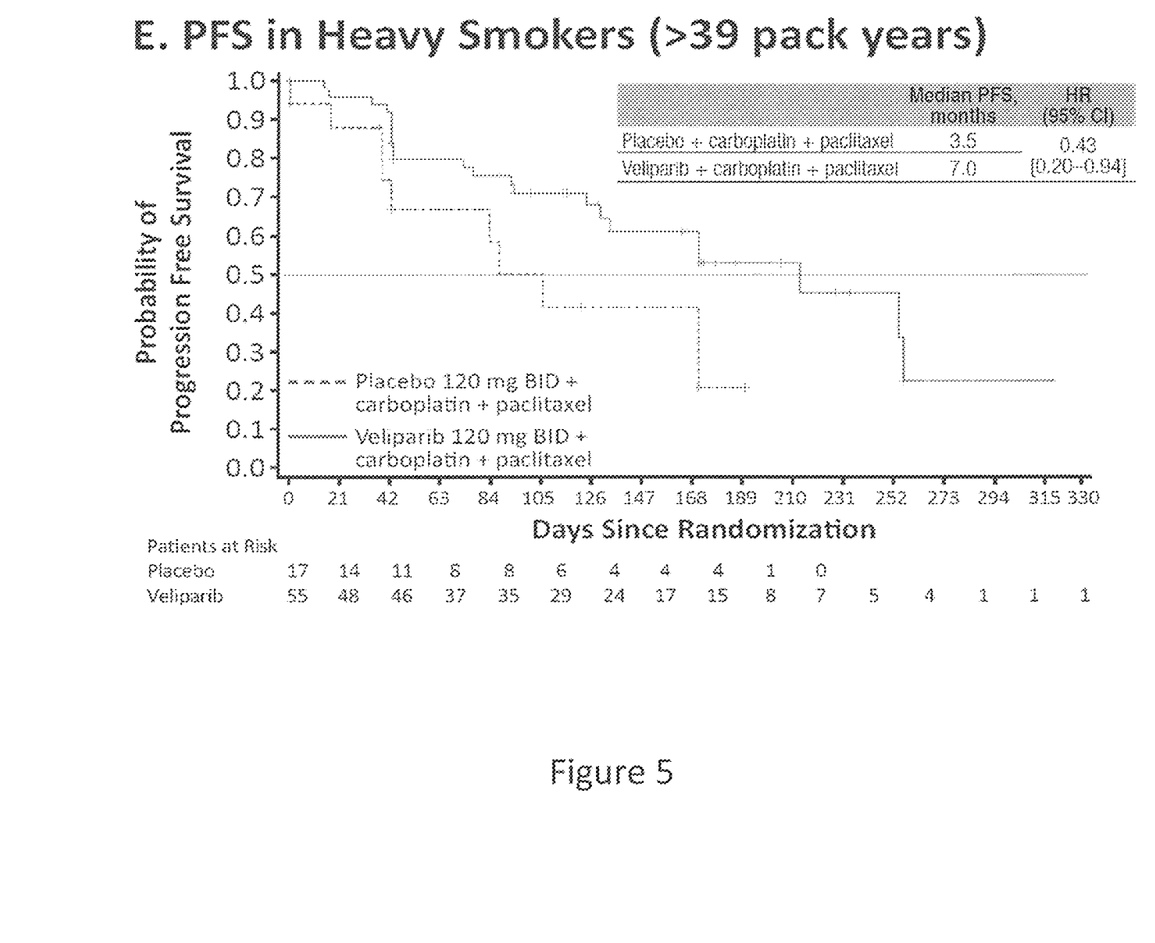
FIG. 5 shows progression-free survival (PFS) in heavy smokers, placebo vs. veliparib, in human subjects.
Figure 6:
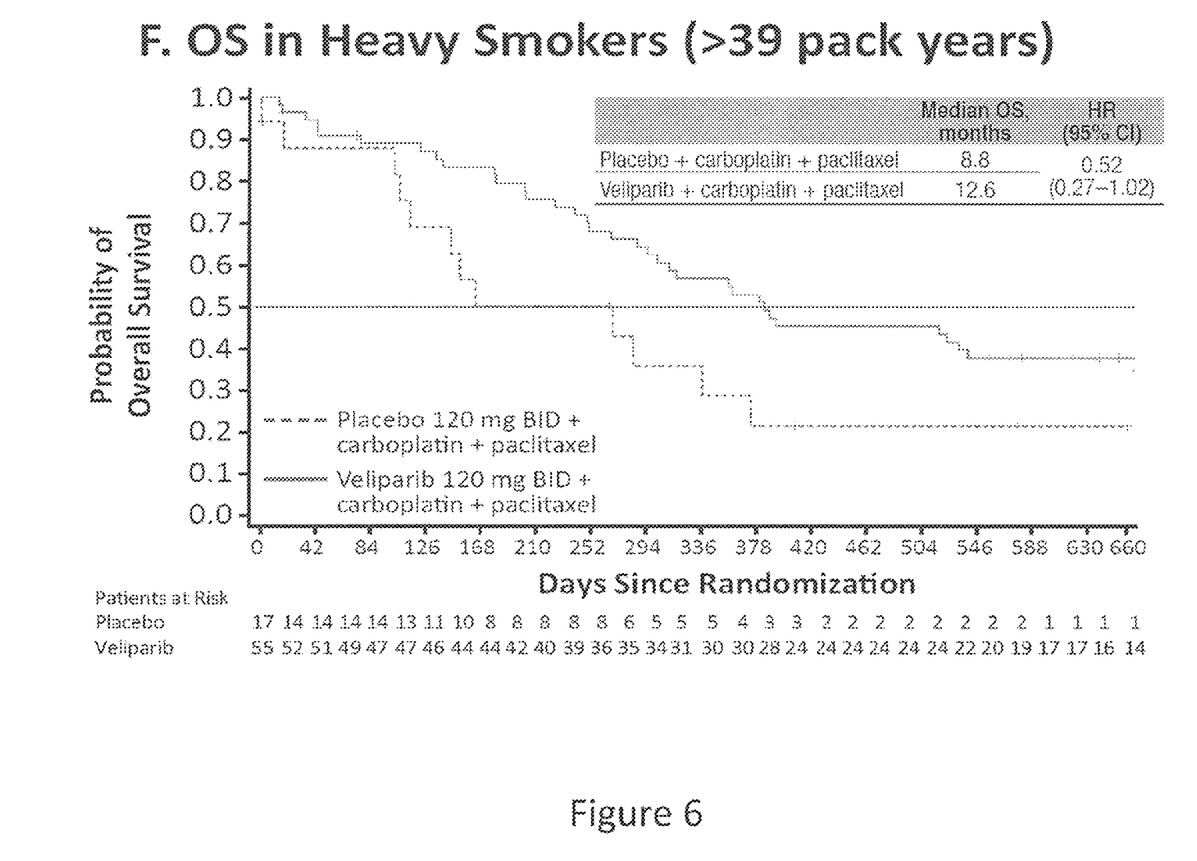
FIG. 6 shows overall survival (OS) in heavy smokers, placebo vs. veliparib, in human subjects.

Patients who were current smokers (defined as having ≥100 smoking events in lifetime and smoking within one year prior to study entry) had statistically significant improvements in progression free survival and overall survival (see FIGS. 1 and 2, unadjusted hazard ratios). Improvements of this magnitude were not seen in any other pre-specified subgroups.

Additional factors possibly predictive of favorable outcomes with veliparib/carboplatin/paclitaxel (VCP) vs carboplatin/paclitaxel (CP) were explored using a multivariate Cox proportional hazards model. These factors included smoking status (current, former, never), histology (squamous, non-squamous), age (<65, ≥65), ECOG (0, 1), gender (female, male), and geographic region (West Europe/ Americas, East Europe/Russia). Test for interaction was performed within the multivariate model.

Factors associated with improved PFS or OS (p<0.10) with veliparib/carboplatin/paclitaxel from a univariate analysis were current smoking, male gender, age <65, ECOG grade 1, eastern region, and squamous histology (Table 2). The multivariate Cox PH analysis including the above factors identified current smoking as the single most predictive factor for improved PFS (VCP/CP HR 0.409, p=0.040) and OS (VCP/CP HR 0.454, p=0.038).

TABLE 2

Efficacy (Univariate Model)

| Subgroup (N for VCP, CP) | PFS VCP/CP HR (95% CI) | p-value | OS VCP/CP HR (95% CI) | p-value |
|---|---|---|---|---|
| Current smoker (64, 31) | 0.39 (0.22-0.68) | 0.0009 | 0.44 (0.27-0.72) | 0.001 |
| Male gender (75, 32) | 0.48 (0.28-0.83) | 0.0082 | 0.67 (0.42-1.07) | 0.0912 |
| Age <65 years (62, 30) | 0.51 (0.29-0.90) | 0.0203 | 0.71 (0.43-1.16) | 0.2492 |
| ECOG = 1 (70, 36) | 0.61 (0.36-1.03) | 0.064 | 0.69 (0.44-1.07) | 0.0994 |
| Eastern region (64, 31) | 0.58 (0.32-1.07) | 0.0794 | 0.75- (0.46-1.24) | 0.2696 |
| Squamous histology (51, 25) | 0.52 (0.25-1.10) | 0.0862 | 0.73 (0.43-1.25) | 0.2492 |

Multivariate modeling suggests that current smoking is strongly associated with improved outcome with veliparib, and other univariate associations may be due to smoking in patients with those characteristics.

The benefit of veliparib that was seen in self-reported current smokers was also observed in patients with chemical evidence of smoking (all patients with cotinine >10 ng/mL) and in heavy smokers (≥39 pack-years among current and former smokers). (see FIG. 3-6). Pack-years were calculated as patient reported years of smoking times packs per day, and results were reported pack-years above or below the median of 39 pack-years. A similar benefit was not seen in other groups. A HR of 0.966 and 0.921 was observed for PFS and OS, respectively, in patients without chemical evidence of smoking, and a HR of 0.971 and 0.808 was observed for PFS and OS, respectively, in light smokers (<39 pack-years).

Figure 7:
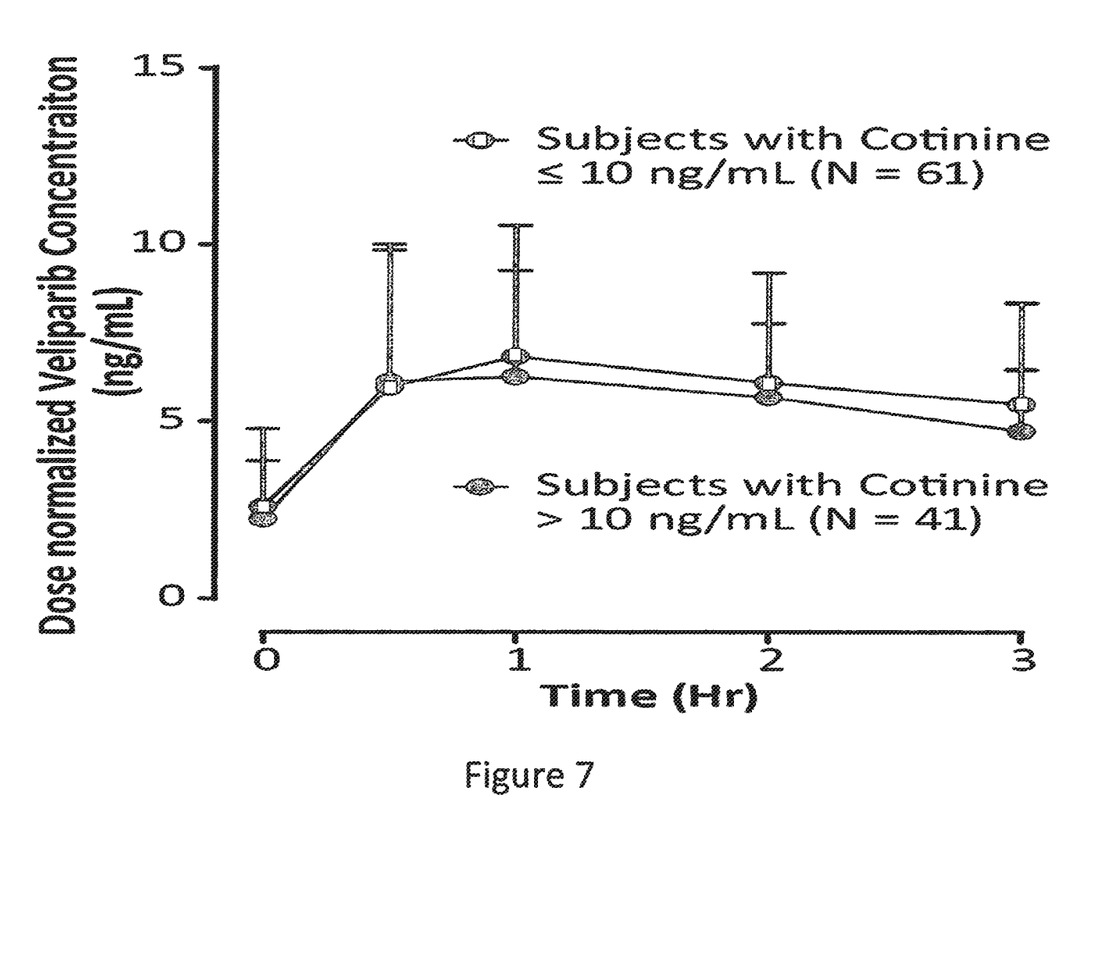
FIG. 7 shows dose normalized veliparib concentration-time profile.

Pharmacokinetic parameters were evaluated for patients with chemical evidence of recent smoking (cotinine high[b], >10 ng/mL) compared with those without evidence of recent smoking (cotinine low, ≤10 ng/mL). There were no significant differences in veliparib PK parameters between the cotinine high and cotinine low patients (see Table 3 and FIG. 7). In addition, no clear differences in carboplatin or paclitaxel levels were identified between cotinine high and cotinine low patients.

TABLE 3

Veliparib Pharmecokinetic Parameters

| Mean ± SD (% CV) | Cotinine Low (≤10 ng/mL) Patients | Cotinine High (>10 ng/mL) Patients |
|---|---|---|
| N | 58[c] | 41 |
| $T_{max}$ (hr) | 1.34 ± 0.95 (71.0) | 1.05 ± 0.82 (78.3) |
| $C_{max}$ (ng/mL/mg) | 8.51 ± 3.21 (37.7) | 7.94 ± 2.90 (36.6) |
| $AUC_{0-12}$ (ng · hr/mL/mg) | 56.9 ± 25.3 (44.5) | 47.8 ± 17.3 (36.2) | b. Pirkle JL, et al, *JAMA*, 1996; 275(16): 1233-1240.
[c]Excludes the patients for whom measurable veliparib concentrations were not available.

These results suggest the PARP inhibition is preferentially beneficial to subjects who have developed lung cancer due to smoking. The benefit provided by veliparib among patients who were smokers was unexpected from prior clinical or pre-clinical studies with veliparib or other PARP inhibitors. A relationship between PARP inhibitor benefit during cancer treatment and smoking has not been previously described in clinical studies. Such a relationship has not been reported in pre-clinical studies, because studies of cancer in animal models do not usually include exposure of animals to tobacco smoke.

Of note, the magnitude of survival benefit for smokers in the Example was unexpectedly large in comparison to recent improvements in lung cancer chemotherapy (shown in Wozniak A J, at al. Randomized trial comparing cisplatin with cisplatin plus vinorelbine in the treatment of advanced non-small-cell lung cancer: a SouthwestOncology Group study. J Clin Oncol. 1998 July; 16(7):2459-65.; Sandier A B, et al. Phase II trial of gemcitabine plus cisplatin versus cisplatin alone in patients with locally advanced or metastatic non-small-cell lung cancer. J Clin Oncol. 2000 January; 8(1):122-30.; Shepherd F A, at al. Erlotinib in previously treated non-small-cell lung cancer. N Engl J Med. 2005; 353(2):123-32.; Sandier A, Gray R, Perry M C, et al. Paclitaxel-carboplatin alone or with bevacizumab for non-small-cell lung cancer. N Engl J Med. 2006; 355(24):2542-50.; Scagliotti G V, Parikh P, von Pawel J, et al. Phase III study comparing cisplatin plus gemcitabine with cisplatin plus pemetrexed in chemotherapy-naive patients with advanced-stage non-small-cell lung cancer. J Clin Oncol. 2008; 26(21):3543-51.) Studies that have led to the adoption of new chemotherapy-based treatments for advanced or metastatic lung cancer in the last 15 years added 1-2 months in median survival to the prior standard (compared to improvement of 7 months in median survival in smokers who participated in the study set forth in the Example above). Thus, the use of PARP inhibitors with chemotherapy for lung cancer or, by extension, to other smoking-related cancers is an important improvement to current standard treatments for smokers.

We claim:

1. A method for the treatment of non-small cell lung cancer in a subject who is a current smoker, comprising administering to the subject an effective amount of a PARP inhibitor in combination with carboplatin and paclitaxel, wherein the PARP inhibitor is 2-[(2R)-2-methylpyrrolidin-2-yl]-1H-benzimidazole-4-carboxamide, or a pharmaceutically acceptable salt thereof.

2. The method of claim 1, wherein the smoker is a heavy smoker.

3. The method of claim 1, wherein the smoker is a cotinine high patient.

4. The method of claim 1, wherein the non-small cell lung cancer is squamous.

5. The method of claim 1, wherein the non-small cell lung cancer is non-squamous.

* * * * *

UNITED STATES PATENT AND TRADEMARK OFFICE
CERTIFICATE OF CORRECTION

| | |
|---|---|
| PATENT NO. | : 9,623,009 B2 |
| APPLICATION NO. | : 14/855621 |
| DATED | : April 18, 2017 |
| INVENTOR(S) | : Giranda et al. |

It is certified that error appears in the above-identified patent and that said Letters Patent is hereby corrected as shown below:

In the Specification

In the Background Of the Invention, Column No: 1, Line(s): 39, "Poly(ADP-ribose)polymerse" to read as --Poly(ADP-ribose)polymerase--

In the Brief Description Of The Drawings, Column No: 2, Line(s): 13-14, "currant smokers," to read as --current smokers--

In the Detailed Description, Column No: 3, Line(s): 26, "per peck" to read as --per pack--

In the Detailed Description, Column No: 6, Line(s): 59, "that ofa subject" to read as --that of a subject--

In the Detailed Description, Column No: 9, Line(s): 47, "-benzimidazole-4-arboxamide," to read as -- -benzimidazole-4-carboxamide,--

In the Detailed Description, Column No: 9, Line(s): 55-56, "-2-yl]-H-benzimidazole-" to read as -- -2-yl]-1H-benzimidazole- --

In the Detailed Description, Column No: 11, Line(s): 4, "part ofa pharmaceutical" to read as --part of a pharmaceutical--

In the Detailed Description, Column No: 11, Line(s): 35, "oxalate, palmoate" to read as --oxalate, pamoate--

In the Detailed Description, Column No: 11, Line(s): 35, "2-napthalesulfonate" to read as --2-napthalenesulfonate--

In the Detailed Description, Column No: 12, Line(s): 12, "hydroxypropylmethyl celluose" to read as --hydroxypropylmethyl cellulose--

Signed and Sealed this
Twentieth Day of November, 2018

Andrei Iancu
*Director of the United States Patent and Trademark Office*

CERTIFICATE OF CORRECTION (continued)

In the Detailed Description, Column No: 14, Line(s): 53, "subjects death." to read as --subject's death.--

In the Detailed Description, Column No: 14, Line(s): 57-58, "data wee censored" to read as --data were censored--

In the Detailed Description, Column No: 16, Table 3, "Veliparib Pharmecokinetie" to read as --Veliparib Pharmacokinetic--